US007483132B2

(12) United States Patent
Du Plessis et al.

(10) Patent No.: US 7,483,132 B2
(45) Date of Patent: Jan. 27, 2009

(54) ANALYSIS OF A MATERIAL IN PARTICULATE FORM

(75) Inventors: Francois Eberhardt Du Plessis, Stellenbosch (ZA); Johannes Coenraad Van Wyk Du Plessis, Kleinmond (ZA)

(73) Assignee: Blue Cude Intellectual Property Company (PTY) Ltd, Strand (ZA)

( * ) Notice: Subject to any disclaimer, the term of this patent is extended or adjusted under 35 U.S.C. 154(b) by 617 days.

(21) Appl. No.: 11/071,462

(22) Filed: Mar. 4, 2005

(65) Prior Publication Data

US 2005/0260763 A1   Nov. 24, 2005

(30) Foreign Application Priority Data

Mar. 11, 2004   (ZA) .................................. 2004/1962

(51) Int. Cl.
*G01J 3/28*  (2006.01)
*G01N 21/00*  (2006.01)

(52) U.S. Cl. ..................... 356/326; 356/244; 356/338

(58) Field of Classification Search ......... 356/244–246, 356/432–436, 337–342, 326, 328
See application file for complete search history.

(56) References Cited

U.S. PATENT DOCUMENTS

| | | | | |
|---|---|---|---|---|
| 4,125,769 A | * | 11/1978 | Marten et al. ................. 378/47 |
| 4,450,576 A | * | 5/1984 | Lubecki et al. ............... 378/47 |
| 5,065,019 A | | 11/1991 | Darilek | |
| 5,133,901 A | * | 7/1992 | Peterson et al. ............. 209/3.2 |
| 5,157,976 A | | 10/1992 | Tokoyama | |
| 5,416,577 A | | 5/1995 | Haggerty | |
| 5,461,229 A | | 10/1995 | Sauter | |
| 5,926,262 A | * | 7/1999 | Jung et al. .................... 356/73 |
| 6,327,899 B1 | | 12/2001 | Diekhans et al. | |
| 6,357,305 B1 | | 3/2002 | Witt et al. | |
| 6,836,325 B2 | * | 12/2004 | Maczura et al. ............. 356/328 |
| 7,113,265 B1 | * | 9/2006 | Sarrazin et al. ............... 356/73 |
| 2004/0012781 A1 | | 1/2004 | Gehrlein et al. | |

FOREIGN PATENT DOCUMENTS

DE   3509671 A1   9/1986

(Continued)

OTHER PUBLICATIONS

U.S. Appl. No. 10/502,300, filed Jul. 22, 2004, Du Plessis.

*Primary Examiner*—L. G Lauchman
(74) *Attorney, Agent, or Firm*—Connolly Bove Lodge & Hutz LLP

(57) ABSTRACT

An apparatus (10) for analyzing material in particulate form is disclosed. The apparatus (10) comprises a vertically elongate housing (12) having an open upper end (26) and a restricted outlet at the lower end. A probe (28) directs light through a transparent cover (22), provided in one wall of the housing (12), and collects light reflected from particulate material in the housing (12). A slide valve (24), which includes a U-shaped section (30) and a T-shaped section (34) with a hole (32) therebetween, partially closes the outlet of the housing (12). Movement of the slide valve (24) by means of a knob (56), rod (36) and coil spring (44) allows for adjustment of the flow rate of the material through the apparatus (10), as well as for clearing blockages which may occur at the exit of the apparatus (10).

9 Claims, 13 Drawing Sheets

FOREIGN PATENT DOCUMENTS

| | | |
|---|---|---|
| DE | 244 821 A1 | 4/1987 |
| DE | 44 14 622 A1 | 10/1995 |
| WO | WO-99/40419 | 8/1999 |
| WO | WO-01/35720 A1 | 5/2001 |
| WO | WO-01/69213 A2 | 9/2001 |

* cited by examiner

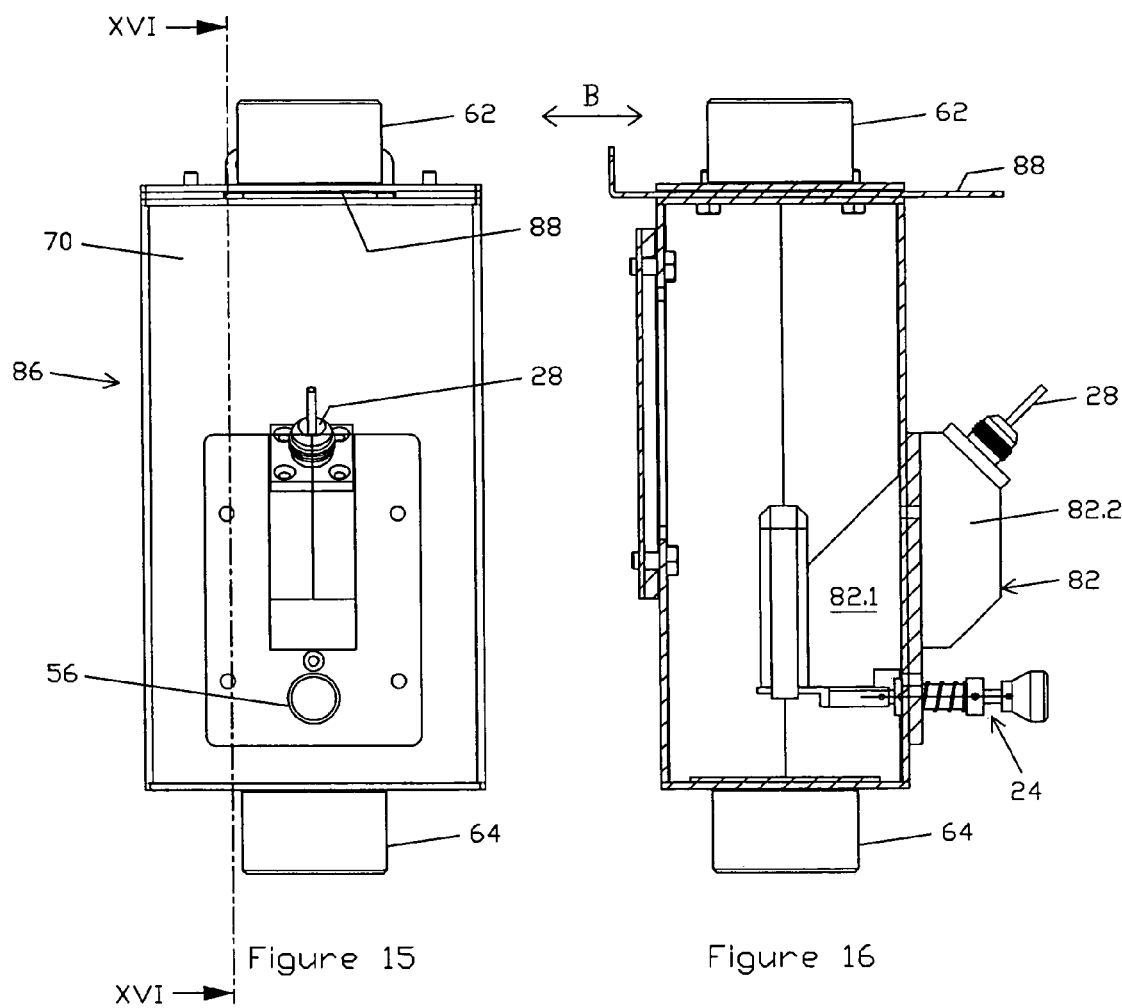

ANALYSIS OF A MATERIAL IN PARTICULATE FORM

CROSS REFERENCE TO RELATED APPLICATIONS

The present application claims priority from South Africa Patent Application No. 2004/1962 filed Mar. 11, 2004.

FIELD OF THE INVENTION

This invention relates to the analysis of a material in particulate form.

BACKGROUND TO THE INVENTION

In the metallurgical industry there is a need to know, as accurately as possible, the composition of the material that has been mined as sand, or mined as rock and then crushed to granular form, and which constitutes the feedstock for a processing plant.

The main reason why this information relating to composition is of vital importance is that the way in which the various operating parameters of the minerals processing plant have to be set depends on the proportions of the constituents in the feedstock. These proportions vary continually as mining progresses through the body of ore being mined, and adjustments thus have to be made to ensure that the plant is being run at maximum efficiency to achieve the best possible yield.

Another reason why this information is of importance is that changes occur in environmental variables such as humidity and temperature, as well as in equipment variables such as supply voltage and the physical condition of the processing plant. Any of these variables may cause certain stages of the process to produce less than optimum intermediate streams of minerals. Ideally these error conditions have to be detected and corrected as soon as possible. Therefore, up-to-date ie. so-called "real time" information on the composition of the mineral being processed is required to ensure that the plant is being run at maximum benefication yield.

The information required for these purposes is obtained by analysing the mineral being processed at various stages of its treatment. The proportions of the constituents as the mineral passes through the processing plant can be used as an indication of the efficiency of the plant and enable adjustments to the process to be made to achieve maximum benefication yield.

Because of a lack of accurate, up-to-date knowledge on the composition of the mineral, and the fear that valuables may be dumped with the discard, plant operators adopt a conservative approach and recycle a proportion of the mineral emerging from some or all of the stages to ensure that the least possible amount of valuables is lost. If accurate real time knowledge on the composition of the mineral beneficated is available, recycling can be reduced without loss of valuable products.

The known methods of determining the proportions of the constituents in the minerals undergoing processing can be divided into "human" and "machine". The main "human" method involves the preparation of a sample, the proportions of the constituents of which are the same as the proportions in the mineral being processed. Obtaining the sample is a lengthy procedure. The first step is to take a number of kilograms of the granular mineral to ensure that the constituents of the sample are as representative as possible of the constituents of the bulk. The sample is split into small portions and then some of these portions recombined until the procedure has eliminated any remaining difference between the proportions in the sample and the proportions in the mineral being processed. The grains in the sample are then identified and counted by a skilled grain counter using a microscope and an optical grid over which the grains are spread.

Another "human" method relies on the skill of the person carrying out the test as it is based on the difference between the colour of the sample being checked and the colour of a standard sample. This is not a particularly accurate method as the human eye cannot pick up small changes in contrast or colour.

The "machine" methods are numerous but these have a number of shortcomings. Some require expensive equipment and, generally, sample preparation is time consuming. Also, some of the equipment is such that it can only be run by trained scientists and even then only in laboratory conditions. Examples of "machine" methods known to the Applicant as at 23 Jan. 2002, as well as a recent development in the spectral analysis of material in particulate form, are described in WO 03/062804.

The present invention seeks to provide a new analysis method and new analysis apparatus which enable real time information on the composition of a material to be obtained.

The method and apparatus of the present invention are primarily intended for use in the processing of minerals but can be used in other industries where the composition of a material must be determined.

BRIEF DESCRIPTION OF THE INVENTION

According to one aspect of the present invention there is provided a method of analysing a material in particulate form which comprises causing the material to flow as a stream into the open upper end of a housing and out of the lower end of the housing, the housing having a restricted outlet and the rate of flow into the housing exceeding the outflow thereby causing material to back-up from the outlet and fill the housing, directing light into the material which is moving downwardly in the housing from the upper end to the lower end, collecting light reflected, from the moving material, and feeding the collected light to a spectrometer.

According to a further aspect of the present invention there is provided apparatus for analysing material in particulate form which comprises a housing having an open upper end and a restricted outlet at the lower end, a transparent cover in one wall of the housing and a probe structure for directing light into the housing through said cover and collecting light reflected from particulate material in the housing.

The apparatus can further include a means such as a slide valve which enables the rate of flow from the housing to be adjusted.

Said slide valve can comprise a section with a hole therein, the section being movable with respect to the housing so as to vary the area of the hole which is within the housing.

The plane in which the inner face of said cover lies can intersect said hole whereby a part of the hole lies inside the housing and a part of the hole lies outside the housing, the part of the hole inside the housing forming said restricted outlet.

Said slide valve can have a forward position in which the hole registers with the housing thereby to open up said slot and allow any material blocking the housing to drop from the housing.

Said open upper end of the housing is preferably bounded by surfaces which intersect to form sharp edges which cut the flowing material and split the flow into a portion that enters the housing and a portion which flows around the housing.

Said sharp edges are bounded between vertical inner surfaces of said housing and further surfaces which are inclined to vertical and which slope downwardly away from said edges.

BRIEF DESCRIPTION OF THE DRAWINGS

For a better understanding of the present invention, and to show how the same may be carried into effect, reference will now be made, by way of example, to the accompanying drawings in which:—

FIG. 15 is a rear elevation of the structure of FIG. 14;

FIG. 16 is a section along the line XVI-XVI of the structure of FIG. 15; and

DETAILED DESCRIPTION OF THE DRAWINGS

Referring firstly to FIGS. 1 to 4, the apparatus is generally designated 10 and comprises a vertically elongate housing 12 which is attached to the side of a casing 14.

Figure 1:
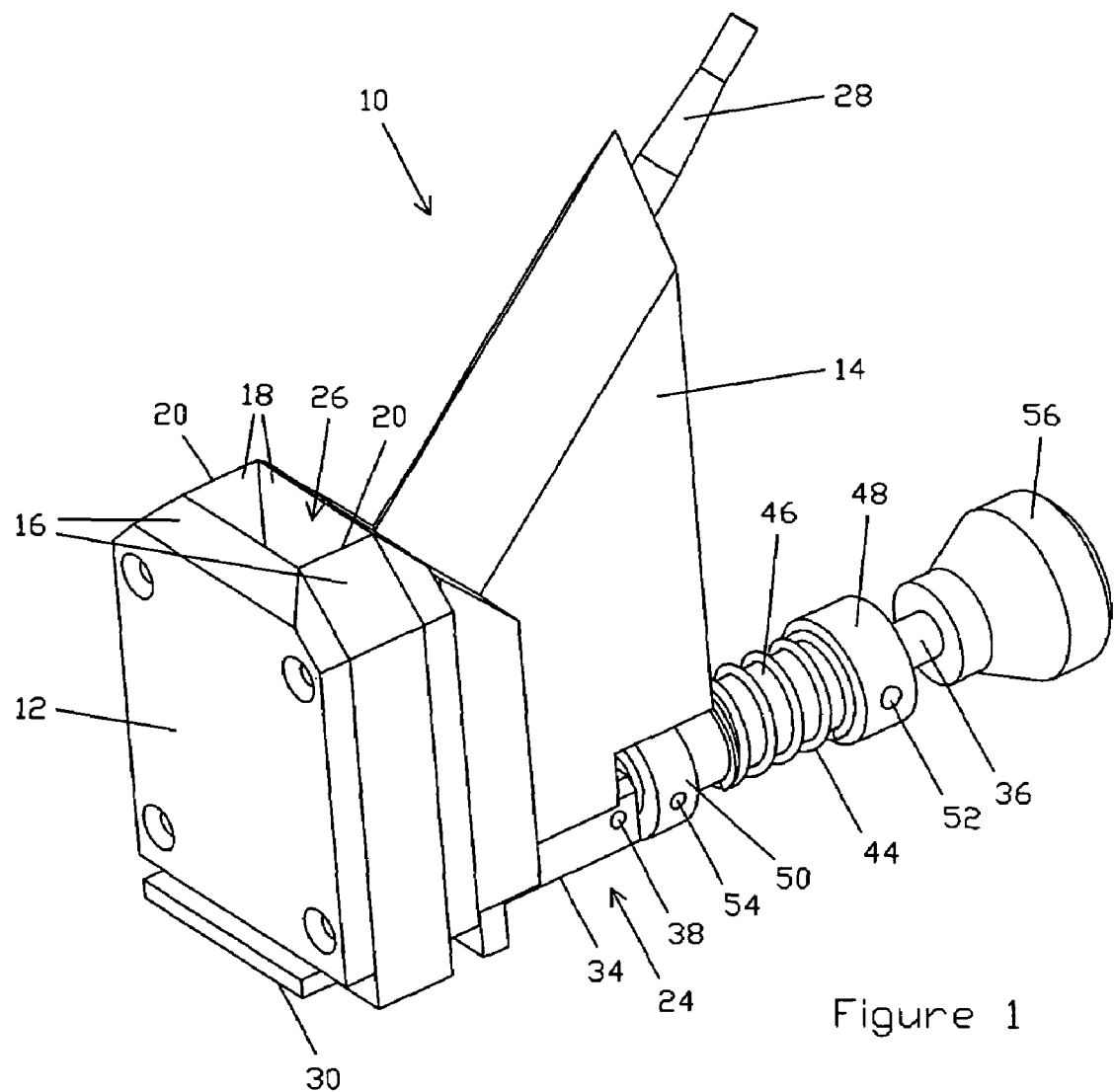
FIG. 1 is a pictorial view of a first embodiment of apparatus for analysing a particulate material.

With specific reference to FIG. 1, the upper edge of the housing 12 is chamfered to provide inclined upper surfaces 16 which intersect the internal surfaces 18 of the housing 12 thereby to define sharp edges 20. More specifically, the internal surfaces 18 of the housing 12 are vertical and intersect the surfaces 16 which slope downwardly and outwardly away from their lines of intersection with the surfaces 18.

The housing 12 has an opening in one side wall thereof, the opening having a transparent cover 22 (FIGS. 3 & 4) of wear resistant material fitted into it.

The lower end of the housing 12 is partially closed by a slide valve 24 (FIG. 5) and the upper end of the housing 12 is open at 26.

Figure 6:
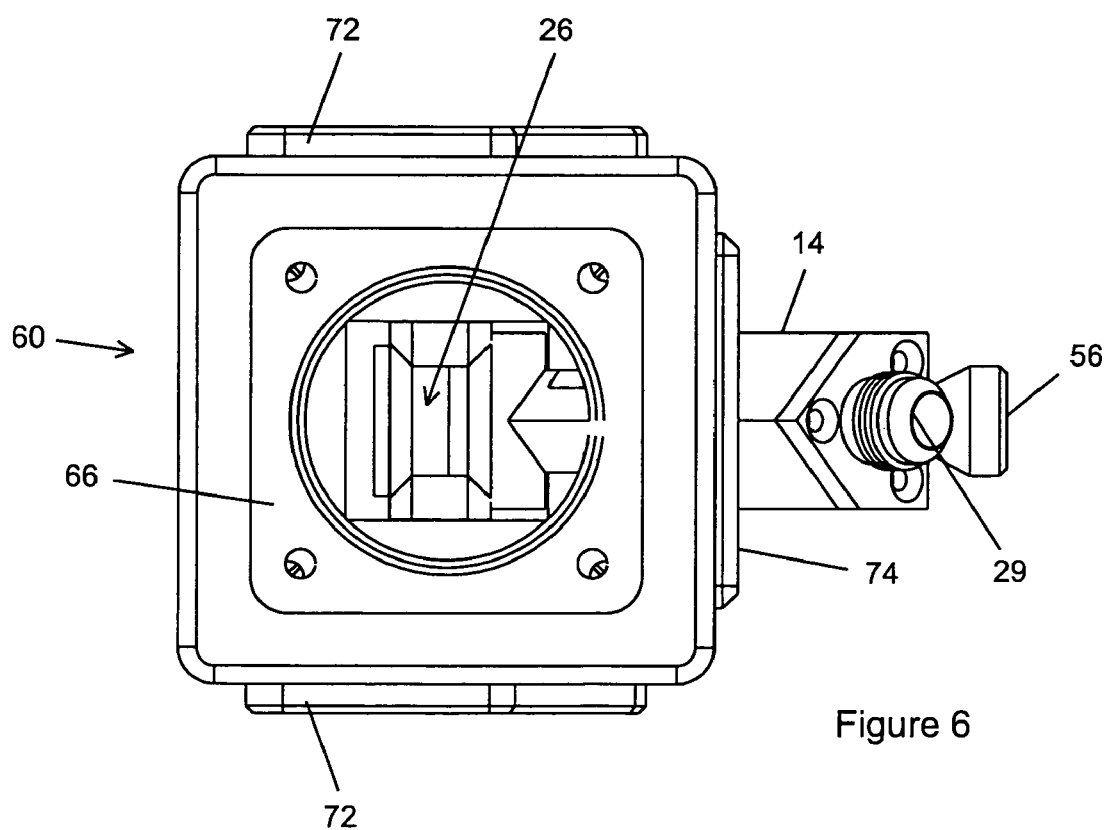
FIG. 6 is a top plan view of a structure, including the apparatus of FIGS. 1 to 4 and the slide valve and operating mechanism of FIG. 5, for mounting in a flow pipe.
Figure 7:
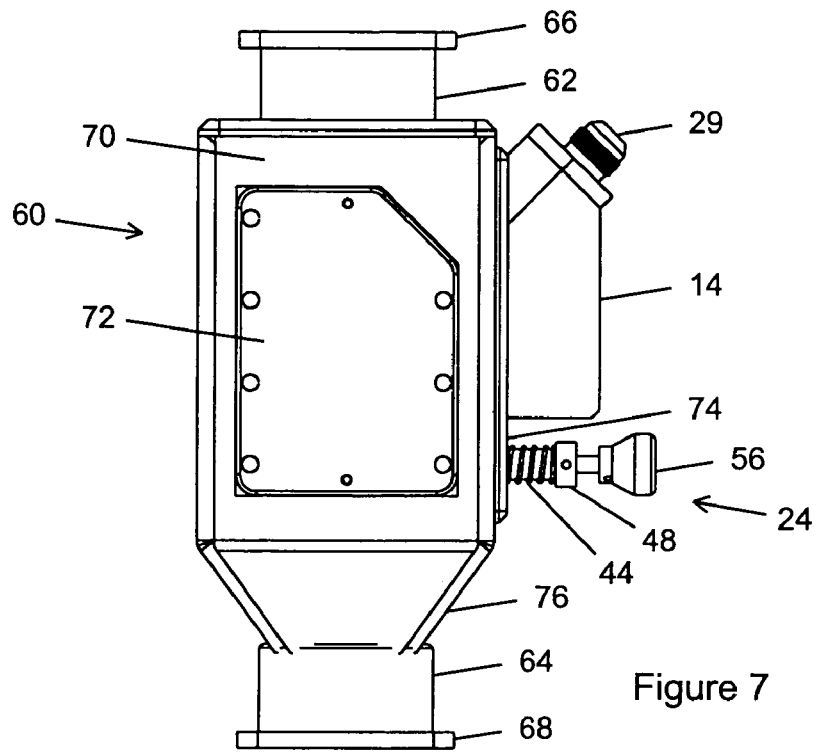
FIG. 7 is a side elevation of the structure of FIG. 6.
Figure 8:
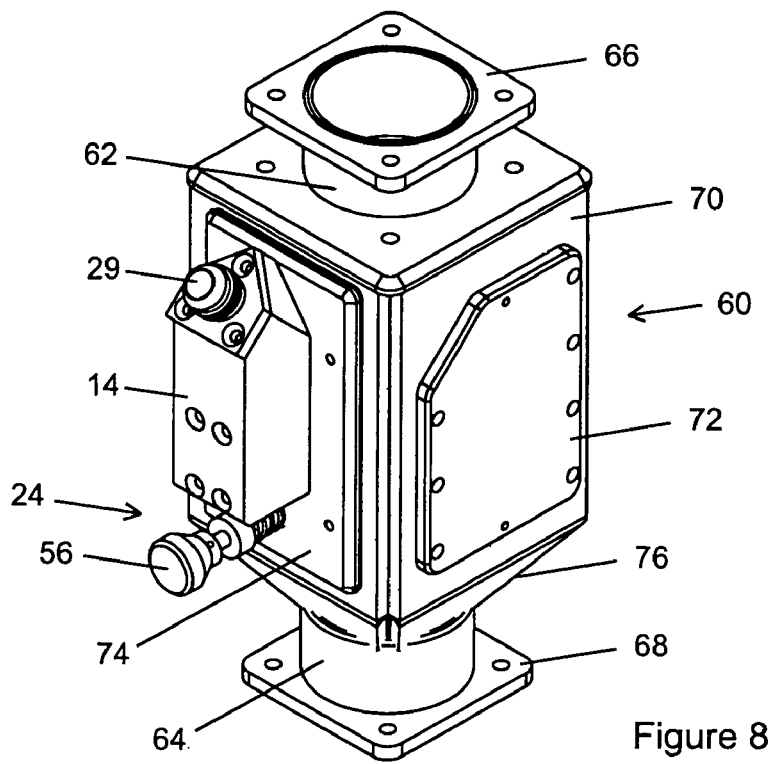
FIG. 8 is a pictorial view of the structure of FIGS. 6 and 7.
Figure 9:
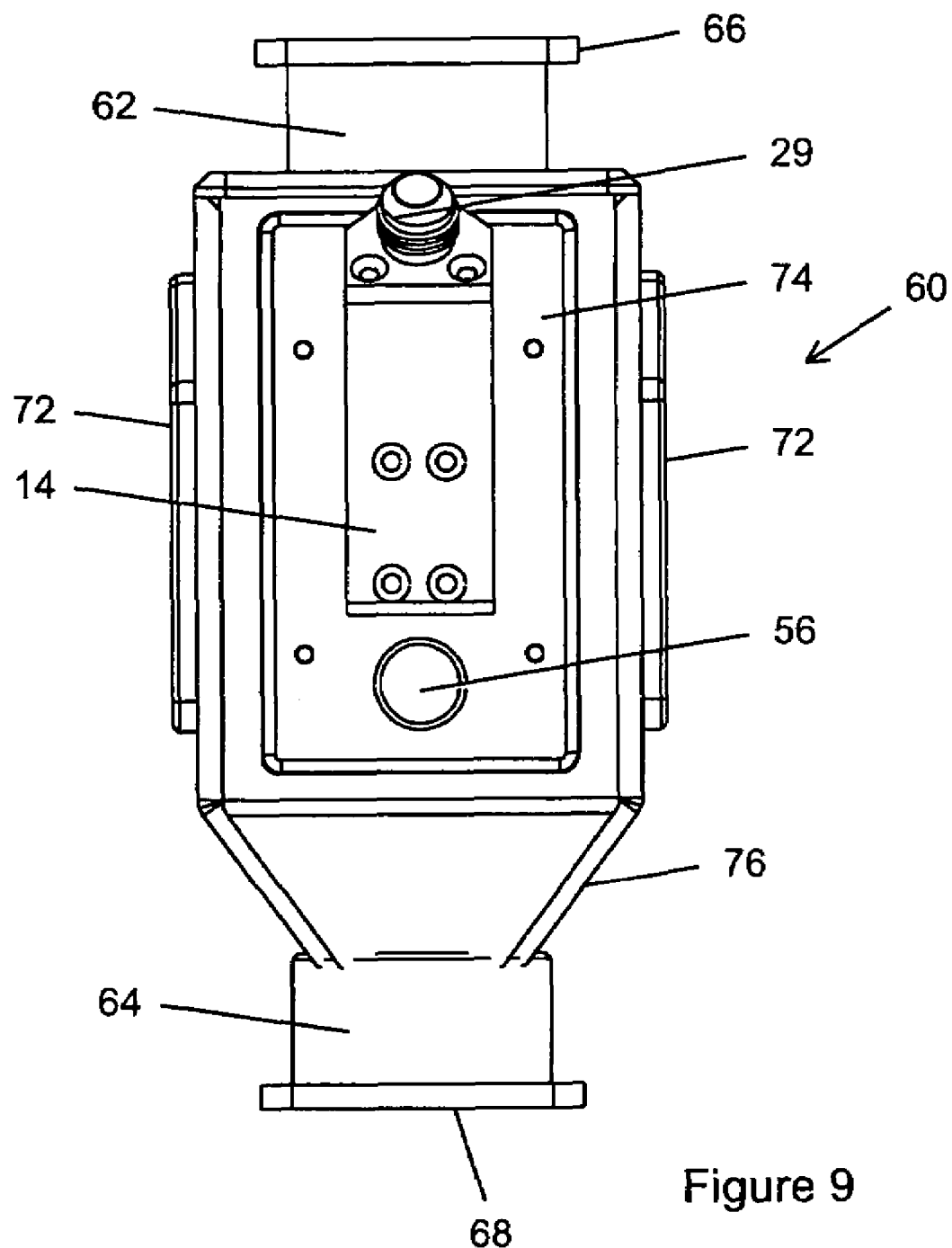
FIG. 9 is a rear elevation of the structure of FIGS. 6 to 8.
Figure 10:
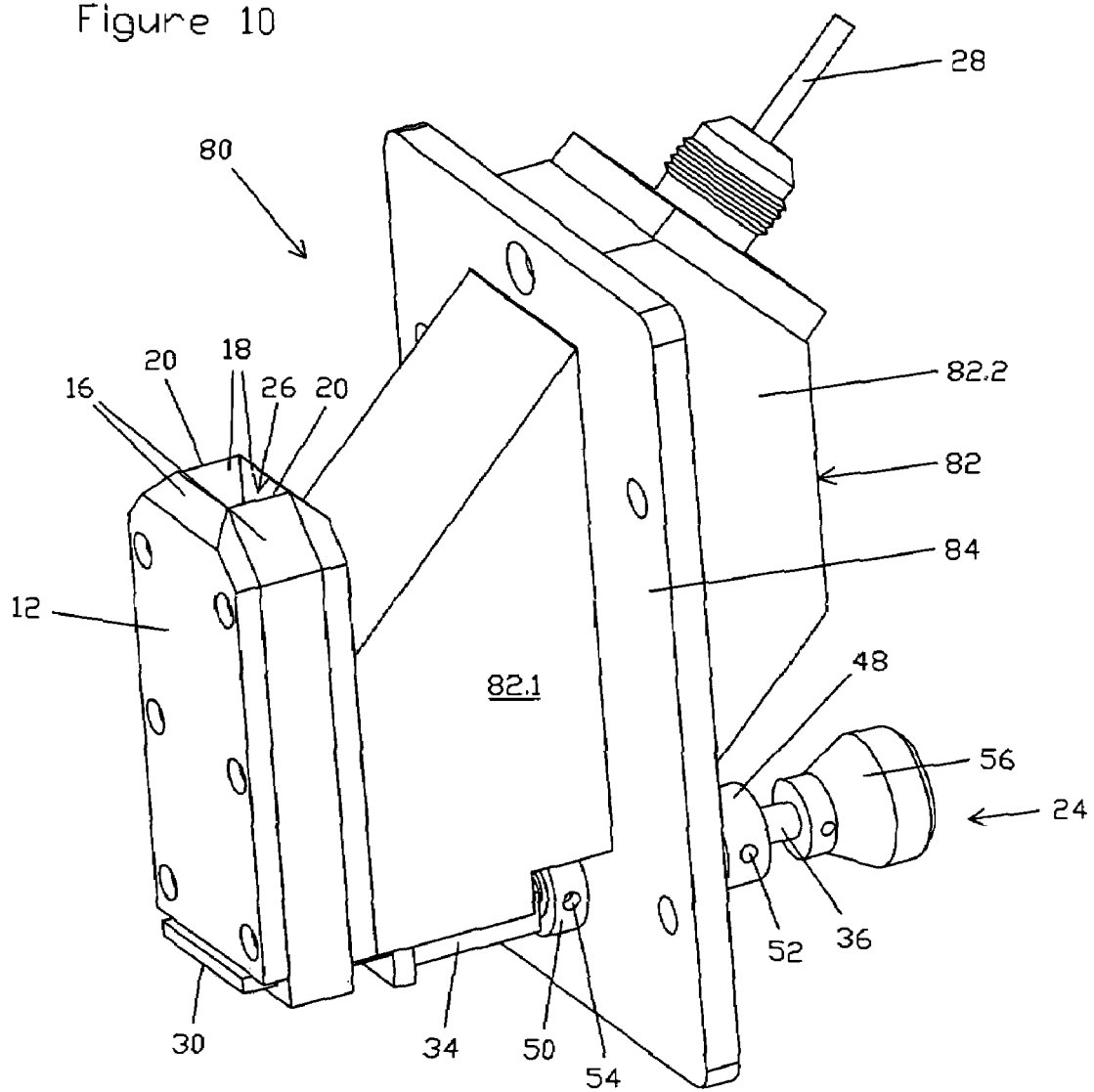
FIG. 10 is a pictorial view of a second embodiment of apparatus for analysing a particulate material.
Figure 11:
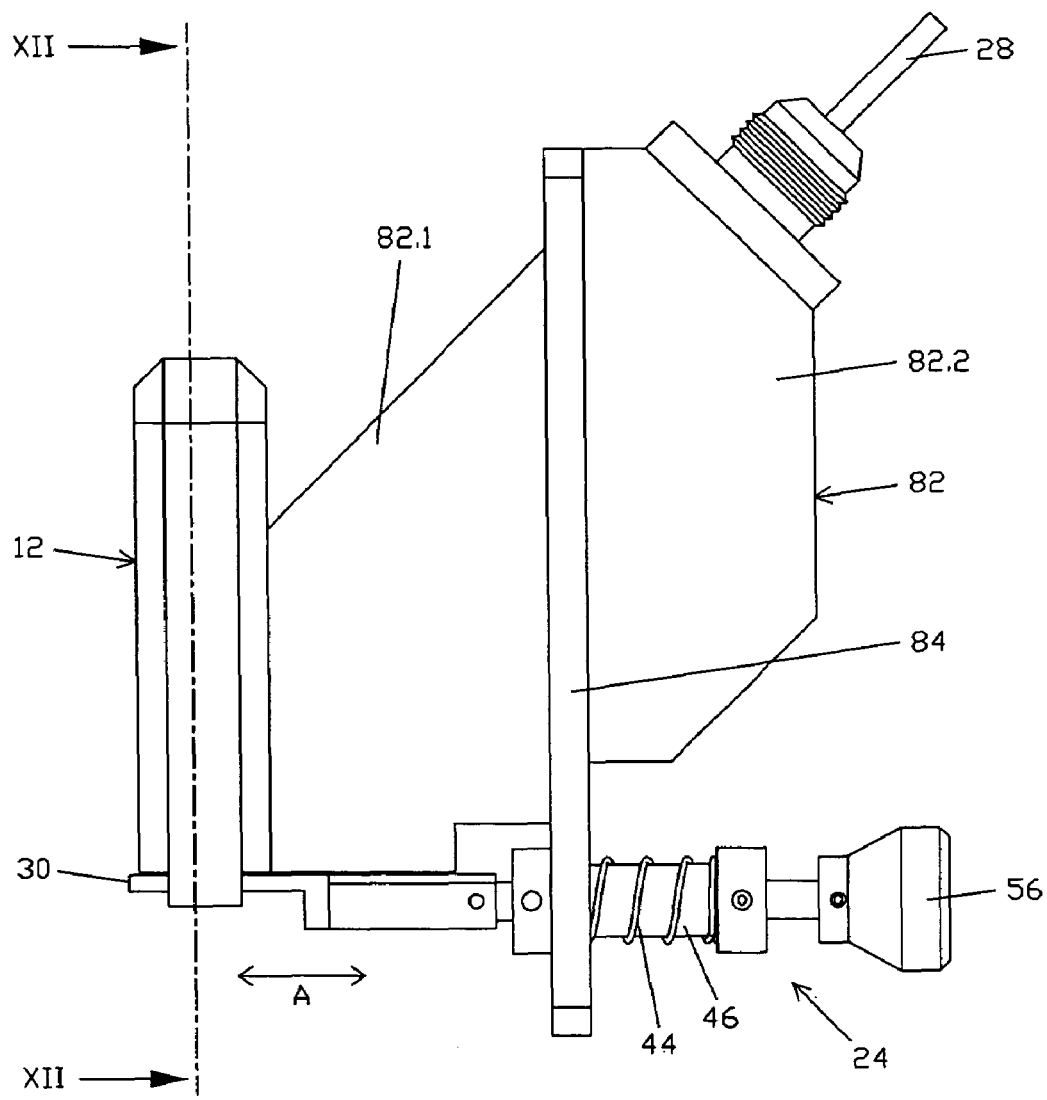
FIG. 11 is a side elevation of the apparatus of FIG. 10.
Figure 12:
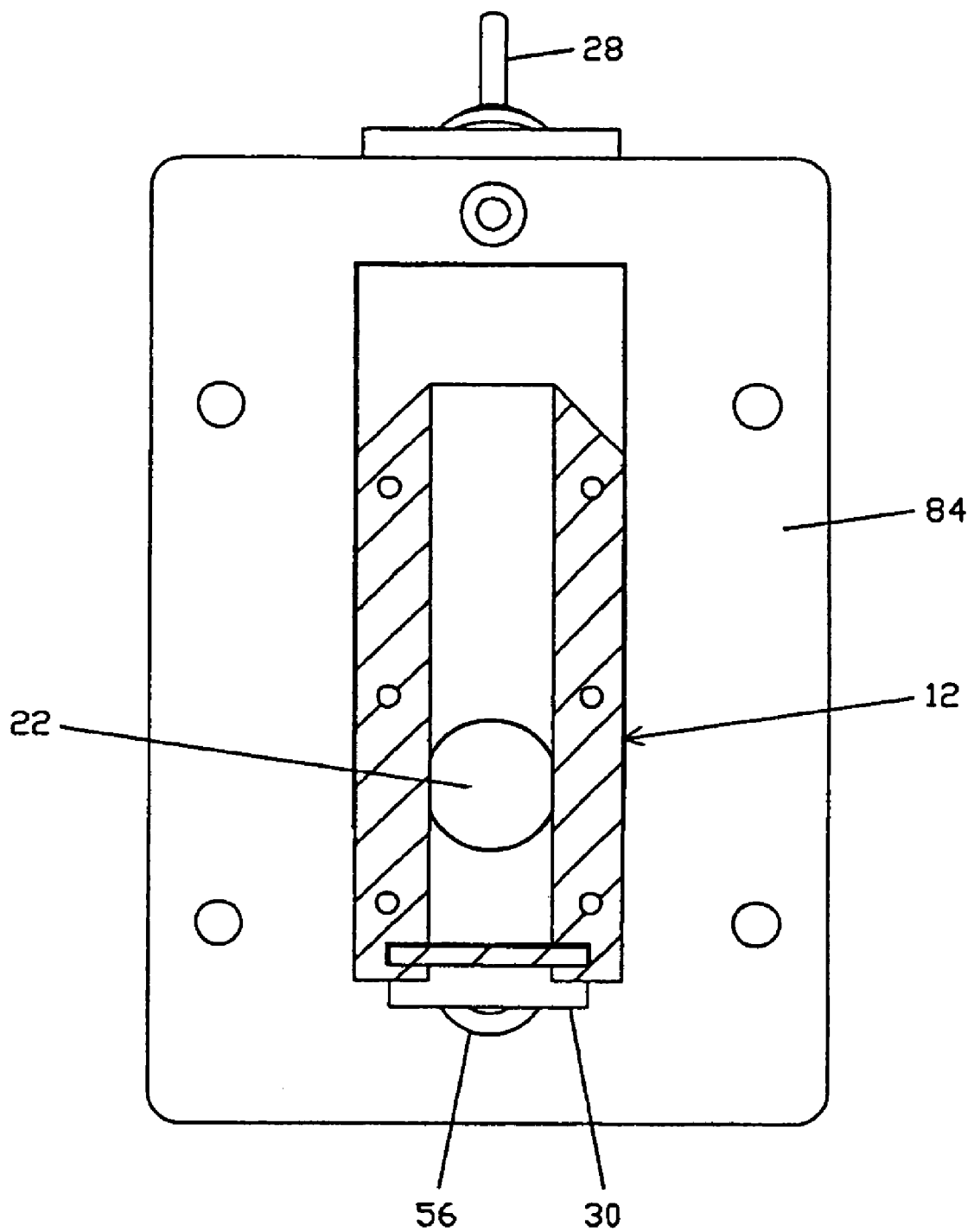
FIG. 12 is a section along the line XII-XII of the apparatus of FIG. 11.
Figure 13:
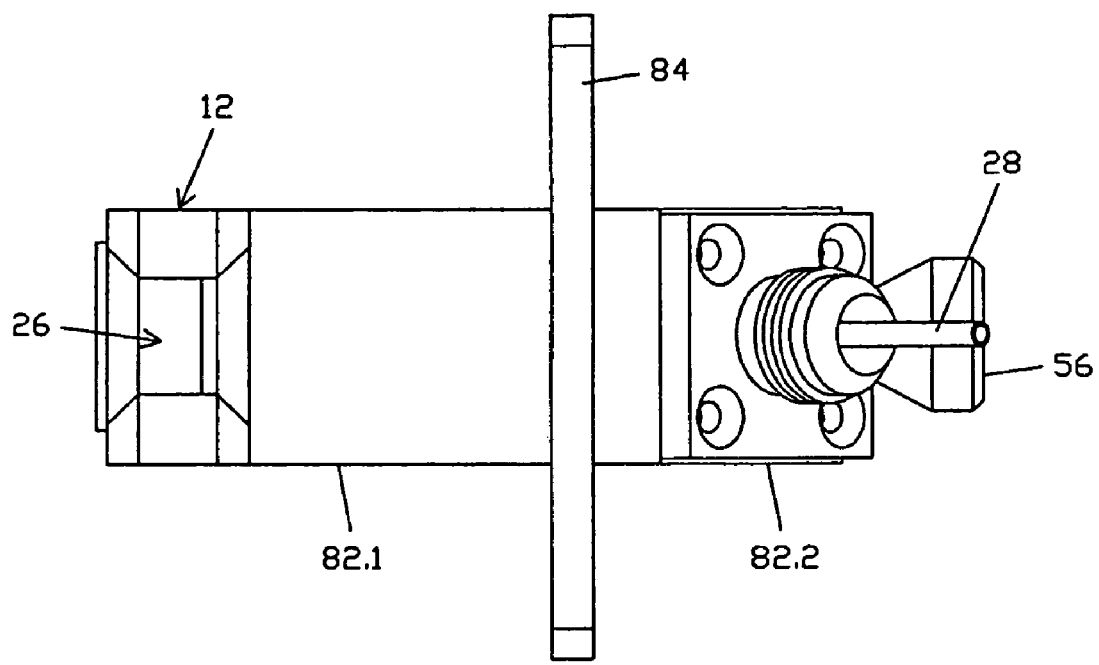
FIG. 13 is a top plan view of the apparatus of FIGS. 10 to 12.

A probe 28 (see FIGS. 1 to 4) protrudes from the casing 14 through a probe mounting 29 (see FIGS. 6 to 8). The probe 28 slopes at an angle of between 30 and 60 degrees with respect to the horizontal. The probe 28 comprises one or more optical fibres for directing light through the cover 22 and into the housing 12, and one or more further optical fibres for collecting reflected light and feeding it to a spectrometer (not shown). The spectrometer is connected to an optical cable (not shown) which is itself connected to the probe 28. It will be understood that the probe structure can comprise a first probe for directing light through the cover 22 and a second probe for receiving reflected light.

Figure 5:
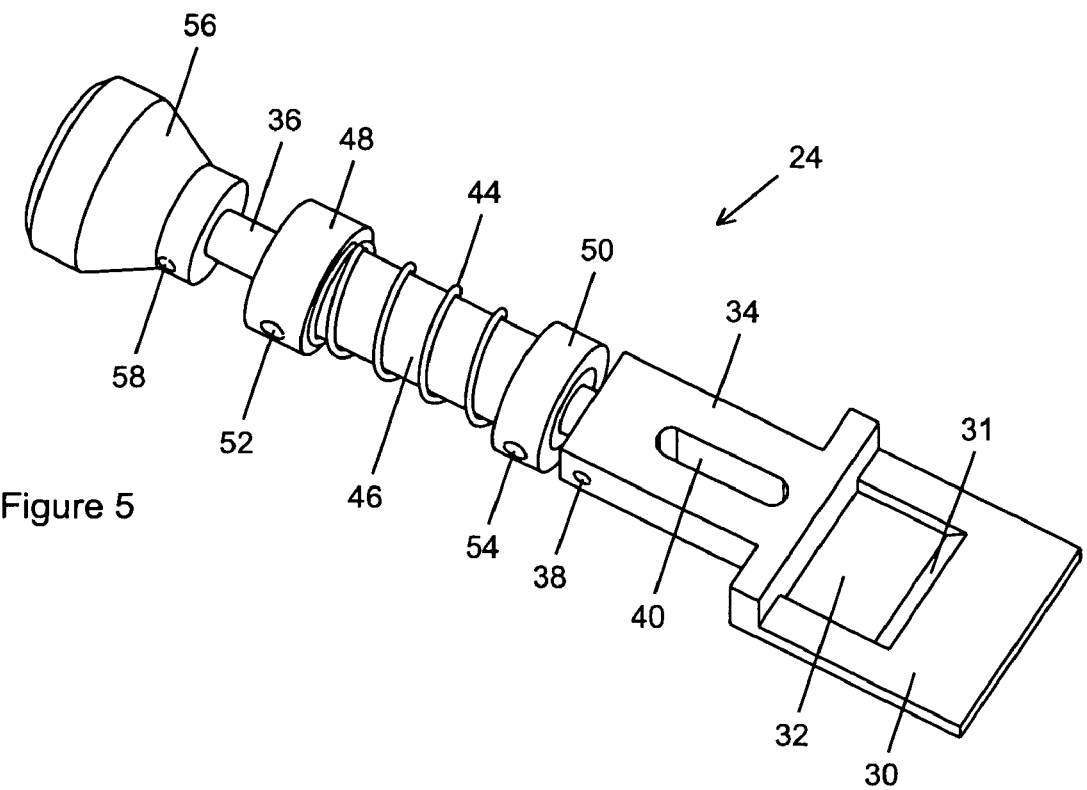
FIG. 5 is an isometric view from underneath of a slide valve and the operating mechanism of the slide valve.

Referring specifically to FIG. 5, the slide valve 24 comprises a U-shaped section 30 having a rectangular hole 32 in it. The section 30 is integral with a T-shaped section 34. A rod 36, forming part of the operating mechanism of the slide valve 24, is secured to the T-shaped section 34 by means of a grub screw 38. An elongate slot 40 is provided in the T-shaped section 34 for receiving a bolt 42 (see FIG. 2), which screws into a tapped bore in the base plate of the casing 14. The front edge of the U-shaped section 30 bounding the hole 32 has a chamfered inner lip 31, as can be seen in FIG. 5, to assist in preventing build-up and blockage of material flowing through the hole 32.

The rod 36 passes through a coil spring 44 and through a sleeve 46. The sleeve 46 has a flange 48 at one end and a removable collar 50 at the other end. A grub screw 52 releasably secures the flange 48 to the rod 36. A further grub screw 54 secures the collar 50 to the sleeve 46. A knob 56 is attached to the rod 36 by means of another grub screw 58. The slide valve 24 can be adjusted back and forth by means of the rod 36 to which the knob 56 is attached. Movement of the slide valve 24 is as shown by arrow A in FIG. 2.

Turning now to FIGS. 6 to 9, the structure illustrated is generally designated 60 and comprises two short pipes 62, 64, two flanges 66, 68 which enable it to be bolted into a pipe line, and walling generally designated 70 which defines an analysis chamber. The pipe 62 forms the inlet to the chamber and the pipe 64 the outlet from the chamber.

The walling 70 includes two removable plates 72 so that conditions within the chamber can be inspected. The plates 72 can be transparent.

The walling 70 further includes a plate 74 by means of which the casing 14 is attached to the remainder of the walling 70. The housing 12 is within the analysis chamber, the open upper end 26 of the housing 12 being aligned with the inlet pipe 62 (see FIG. 6).

A downwardly tapering cone 76 (FIGS. 7 to 9) forms a passageway between the analysis chamber bounded by the walling 70 and the pipe 64.

Figure 2:
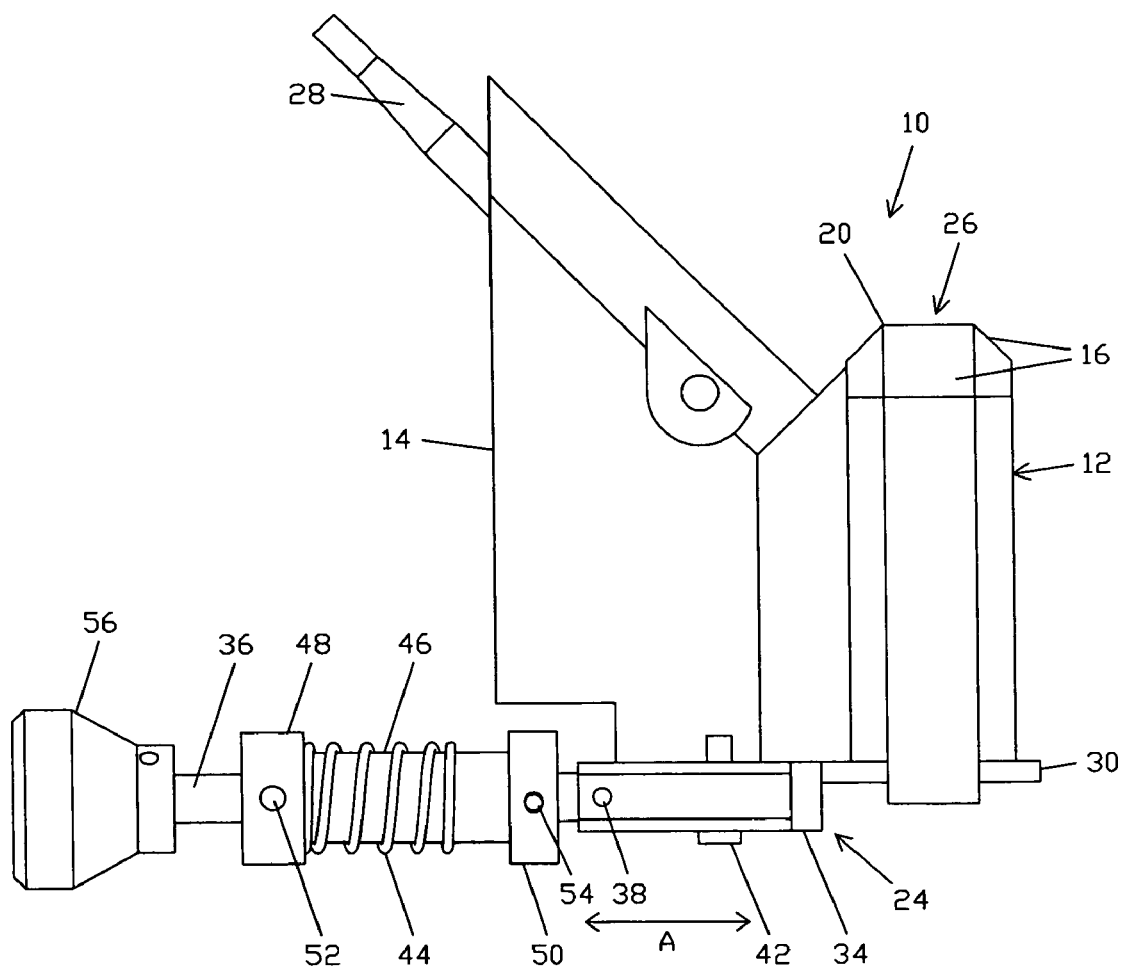
FIG. 2 is a side elevation of the apparatus of FIG. 1.
Figure 3:
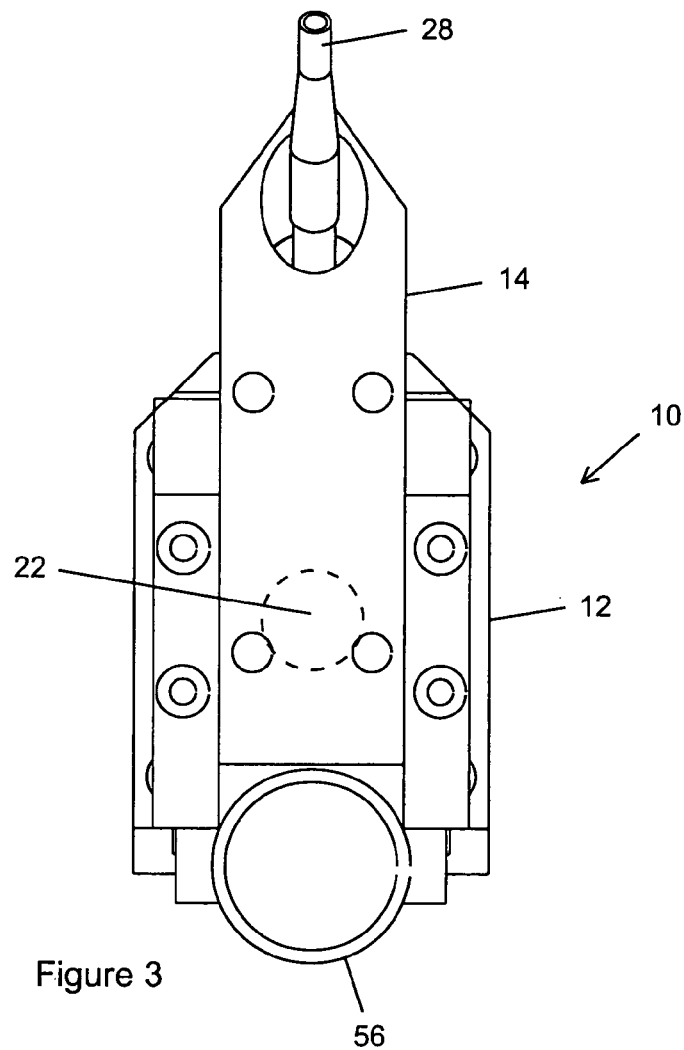
FIG. 3 is a rear elevation of the apparatus of FIGS. 1 and 2.
Figure 4:
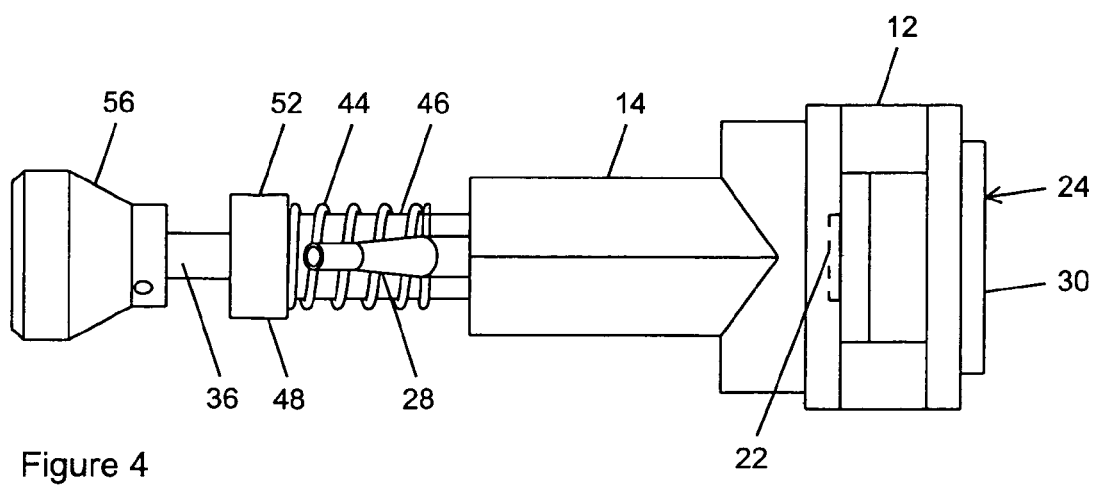
FIG. 4 is a top plan view of the apparatus of FIGS. 1 to 3.

To assemble the slide valve 24 and its operating mechanism the rod 36 is pushed, from right to left in FIG. 7, through a hole in the plate 74. The plate 74 is at this time detached from the remainder of the walling 70. The sleeve 46 and then the spring 44 are slid onto the rod 36 and the sleeve 46 secured by the grub screw 52. The sleeve 46 passes through the hole in the plate 74 and the collar 50 is re-secured to the sleeve 46, on the end thereof which will be inside the chamber, by fastening the grub screw 54. The spring 44 pushes the sleeve 46 and rod 36 to the right as viewed in FIG. 7 so that the collar 50 abuts the inside face of the plate 74. The knob 56 is then secured to the rod 36 by means of the grub screw 58 and the slide valve 24 is secured to the casing 14 by means of the bolt 42 which passes through the elongate slot 40. The bolt 42 cooperates with the slot 40 to allow the slide valve 24 to be releasably attached to the casing 14 whilst allowing the slide valve 24 to be slid, back and forth, as indicated by the double-headed arrow A (FIG. 2). The plate 74 is then attached to the remainder of the walling 70.

It will be understood that by releasing the sleeve 46 from the rod 36 and sliding the rod 36 through the sleeve 46, the position of the rod 36, and hence of the valve 24, can be adjusted. The sleeve 46 is then re-secured to the rod 36. Thus the position of the sleeve 46 with respect to the plate 74 does not change, but the section 30 has been displaced with respect to the housing 12.

In operation, the U-shaped section 30 of the slide valve 24 is in the lower part of the housing 12. The rectangular hole 32 between the U-shaped section 30 and the T-shaped section 34 of the slide valve 24 protrudes just beyond the wall of the housing 12 which has the cover 22 in it. The area of the hole 32 which is beyond this wall is thus within the area bounded by the housing 12 and forms a slot through which material that has entered the housing 12 from above can exit from the housing 12.

Particulate material flowing in through the pipe 62 piles up in the housing 12 and surplus material flows around the housing 12 to the outlet pipe 64.

To clear a blockage, the knob 56 is pushed to the right, as viewed in FIG. 2. This compresses the spring 44 and moves the slide valve 24 to a position in which the hole 32 is in register with the housing 12. This enables any material blocking the outlet slot to fall out of the bottom of the housing 12. When the knob 56 is released the spring 44 pushes on the flange 48 and moves the slide valve 24 back to its operative position in which the collar 50 is against the plate 74.

In operation, the mineral or other material to be spectrographically analysed flows into the upper end of the housing 12 through the opening 26 at a rate which exceeds the rate at which it can flow out of the housing 12 through the slot. The housing 12 thus fills up and surplus material simply flows down the outside of the housing 12.

There is a flow of material through the exit slot formed by the hole 32 and the column of material in the housing 12 moves steadily downwardly past the cover 22. Light entering the housing 12 through the cover 22 from the probe 28 is reflected diffusely back off the material, picked up by the collector optical fibres and fed to the spectrometer. The position of the slot ensures that the greatest rate of flow of material is at the side of the housing 12 defined by the cover 22.

Referring now to FIGS. 10 to 13, a further form of apparatus is illustrated and is generally designated 80. Where applicable, the same references numerals as for FIGS. 1 to 9 have been used. The apparatus 80 includes a casing 82, which comprises two sections 82.1, 82.2 separated by a vertically elongate plate 84. The vertical elongate housing 12 is attached to the section 82.1. There is a hole (not shown) in the plate 84 through which the sleeve 46 of the slide valve 24 passes. The assembly and operation of the slide valve 24 within the apparatus 80 is the same as is described above in respect of apparatus 10.

Figure 14:
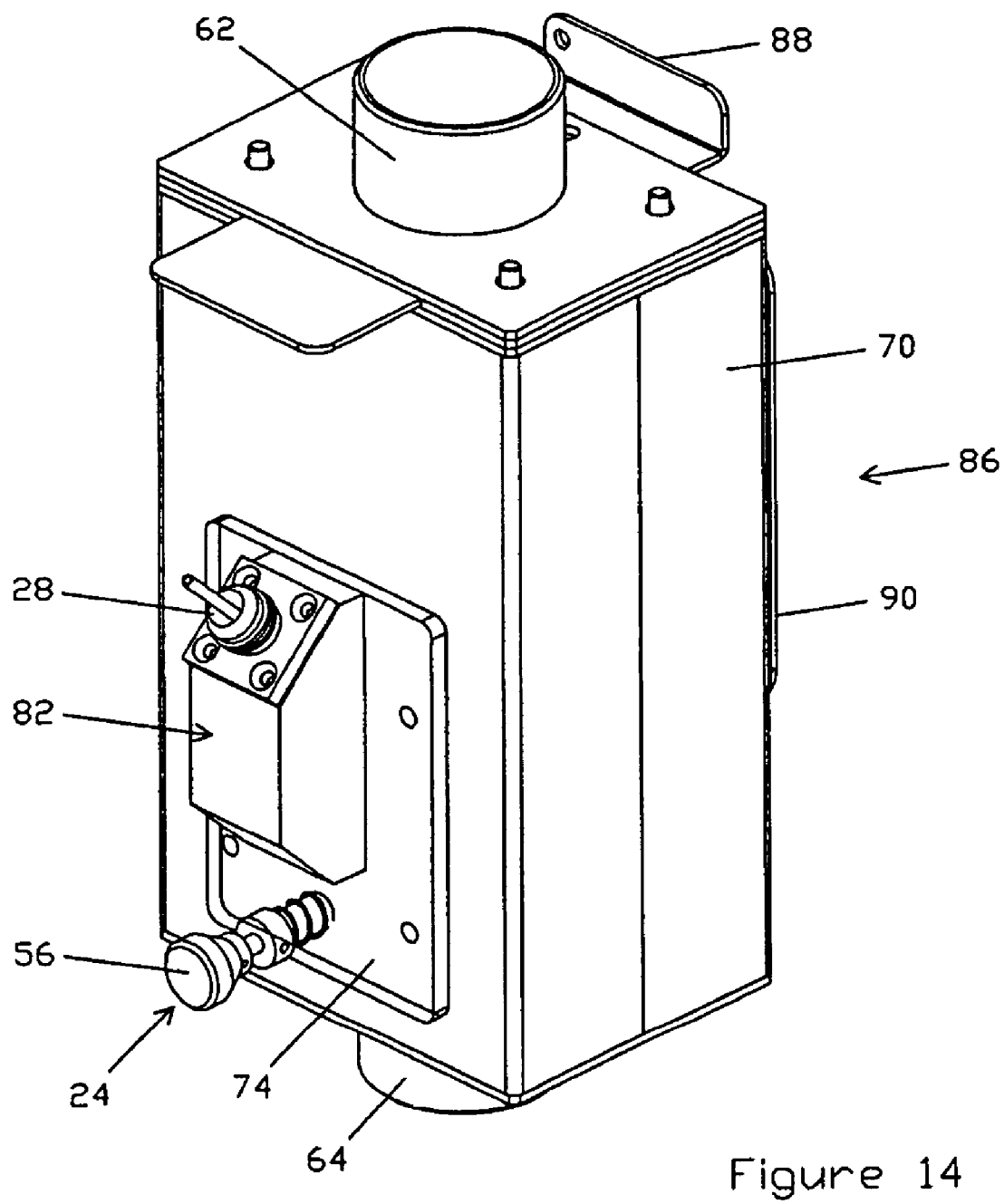
FIG. 14 is a pictorial view of a structure, including the apparatus of FIGS. 10 to 13 and the slide valve and operating mechanism of FIG. 5, for mounting in a flow pipe.

Referring now to FIGS. 14 to 16, the structure illustrated is generally designated 86 and is similar to the structure 60 illustrated in FIGS. 6 to 9. Where applicable, the same reference numerals have been used.

The structure 86 includes an L-shaped shut-off and control valve 88 which can be slid, as shown by the double-headed arrow B in FIG. 16, to adjust flow of the material to be analysed across the cover 22.

Figure 17:
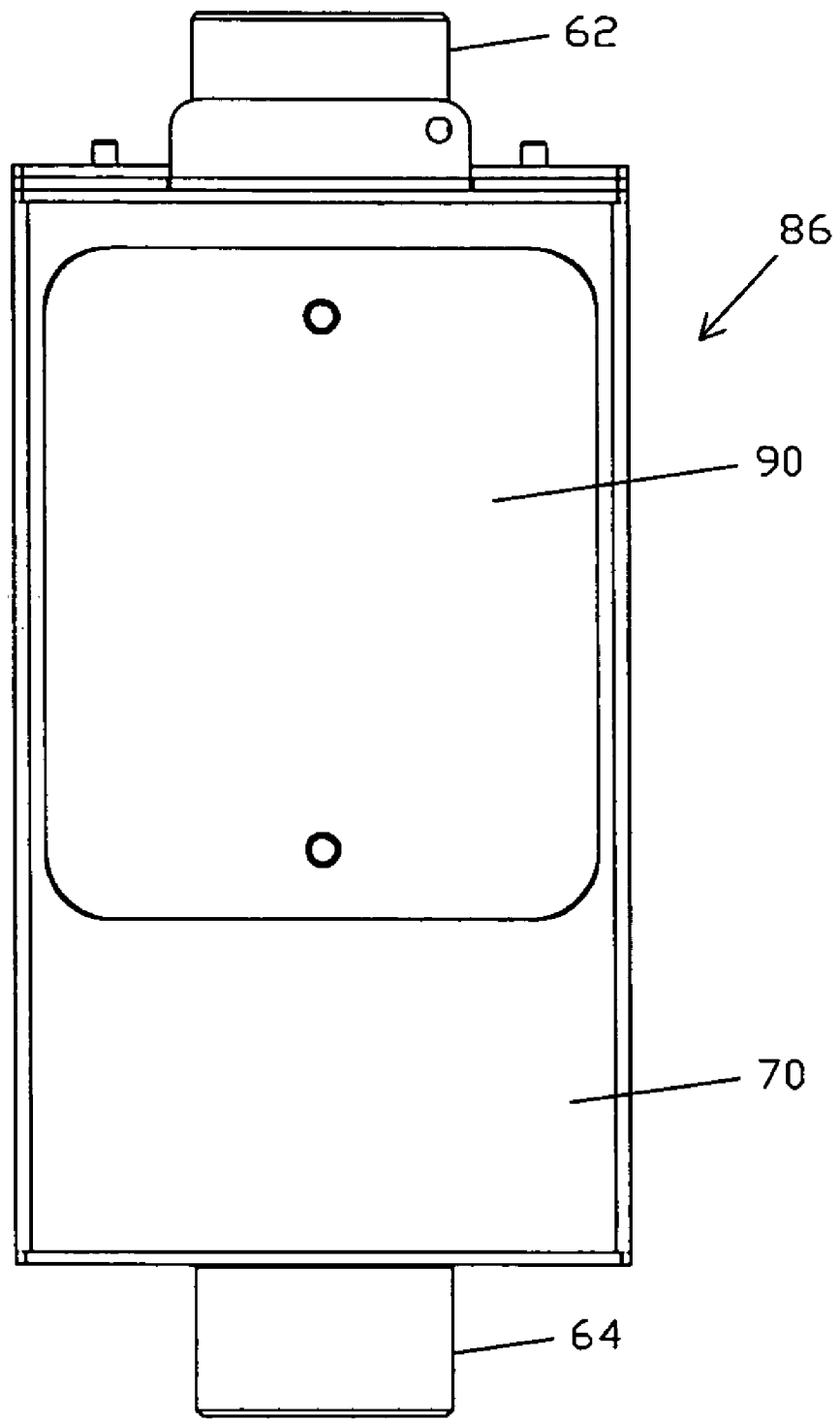
FIG. 17 is a front elevation of the structure of FIGS. 14 and 15.

Furthermore, a removable plate 90 (FIGS. 16 & 17), analogous to the two plates 72 of the structure 60, is attached to the walling 70 so that conditions within the analysis chamber can be inspected. The plate 90 can be transparent.

The assembly and operation of the structure 86 is as described above in relation to the structure 60.

The apparatus 10, structure 60, apparatus 80 and structure 60 have been illustrated and described in the vertical orientation, but may be slightly inclined to the vertical.

The material in particulate form to be analysed by the structures 60 and 86 can be in the form of a dry powder or can be suspended in a liquid so as to form a slurry.

Features of the structures described above are:
1. That the material moves past a transparent cover;
    1.1 to expose a high number of particles during each measurement period;
    1.2 to expose a high number of particle orientations during each measurement period;
    1.3 to average out any strong specular (mirror-like) reflections from any particles.
2. The transparent cover is positioned vertically, or substantially vertically, in order to minimise abrasive forces possibly scratching the transparent cover and causing a loss of transparency.
3. Segregation between different material types and particle sizes comprising the bulk stream is minimized by:
    3.1 cutting a sample from the middle bulk of the stream and avoiding the disturbed sides.
    3.2 cutting in such a way as to minimise the disturbance of the sample falling into the vertically elongate chamber and pushing the rest of the sample outwards by employing an asymmetrical cutting edge at the top.
4. Avoiding the normally occurring pyramid shaped build-up on the top of the chamber by positioning the chamber in a fast-flowing stream, combined with a continuous withdrawal of material downwards through the chamber. The resulting material build-up is therefore concave-shaped and turbulent, avoiding the segregation that occurs on the sides of a convex shape like a pyramid.
5. The optically transparent cover is self-cleaned by the passing material particles to minimize the effect of dust on the transparency of the cover.
6. The optically transparent cover can be either a hard material such as sapphire or a soft polishable polycarbonate to ensure transparency.

The invention claimed is:

1. A method of analyzing a material in particulate form comprising causing the material to flow as a stream into the open upper end of a housing and out of the lower end of the housing, the housing having a restricted outlet and the rate of flow into the housing exceeding the outflow thereby causing material to back-up from the outlet and fill the housing, directing light into the material which is moving downwardly in the housing from the upper end to the lower end, collecting light reflected from the moving material, and feeding the collected light to a spectrometer, said open upper end of the housing having edges and said method comprising cutting the flowing material and splitting the flow into a portion that enters the housing as said stream and a portion which flows around the housing.

2. An apparatus for analyzing material in particulate form which comprises a housing having an open upper end and a restricted outlet at the lower end, a transparent cover in one wall of the housing and a probe structure for directing light into the housing through said cover and collecting light reflected from the particulate material in the housing, wherein said open upper end of the housing is bounded edges which are configured for cutting the flowing material and splitting the flow into a portion that enters the housing and a portion which flows around the housing.

3. The apparatus according to claim 2 and including means to enable the area of the outlet from the housing to be adjusted.

4. The apparatus according to claim 3, wherein said means is a slide valve.

5. The apparatus according to claim 4, wherein said slide valve comprises a section with a hole therein, the section being movable with respect to the housing so as to vary the area of the hole which is within the housing.

6. The apparatus according to claim 5, wherein the plane in which the inner face of said cover lies intersects said hole whereby a part of the hole lies inside the housing and a part of the hole lies outside the housing, the part of the hole inside the housing forming said restricted outlet.

7. The apparatus according to claim 6, wherein said slide valve has a forward position in which the hole registers with the housing thereby to open up said slot and allow any material blocking the housing to drop from the housing.

8. The apparatus according to claim 2, wherein said open upper end of the housing is bounded by surfaces which intersect to form said edges.

9. The apparatus according to claim 8, wherein said edges are bounded between vertical inner surfaces of said housing and further surfaces which are inclined to vertical and which slope downwardly away from said edges.

* * * * *

UNITED STATES PATENT AND TRADEMARK OFFICE
CERTIFICATE OF CORRECTION

PATENT NO. : 7,483,132 B2  
APPLICATION NO. : 11/071462  
DATED : January 27, 2009  
INVENTOR(S) : Francois E. Du Plessis et al.

Page 1 of 1

It is certified that error appears in the above-identified patent and that said Letters Patent is hereby corrected as shown below:

On the Title page, Item (73) Assignee: "Blue Cude Intellectual Property Company (PTY) LTD, Strand (ZA)" should read -- Blue Cube Intellectual Property Company (PTY) LTD, Strand (ZA) --.

Signed and Sealed this
Twenty-first Day of June, 2011

David J. Kappos
*Director of the United States Patent and Trademark Office*